(12) United States Patent
Merlin et al.

(10) Patent No.: US 9,717,695 B2
(45) Date of Patent: Aug. 1, 2017

(54) CONSTRUCTS FOR DIAGNOSING AND TREATING INFLAMMATORY BOWEL DISEASES AND COLON CANCER

(71) Applicant: Georgia State University Research Foundation, Inc., Atlanta, GA (US)

(72) Inventors: Didier Merlin, Decatur, GA (US); Bo Xiao, Decatur, GA (US); Hamed Laroui, Decatur, GA (US)

(73) Assignee: Georgia State University Research Foundation, Inc., Atlanta, GA (US)

( * ) Notice: Subject to any disclaimer, the term of this patent is extended or adjusted under 35 U.S.C. 154(b) by 0 days.

(21) Appl. No.: 14/401,957

(22) PCT Filed: May 18, 2013

(86) PCT No.: PCT/US2013/041741
§ 371 (c)(1),
(2) Date: Nov. 18, 2014

(87) PCT Pub. No.: WO2013/173822
PCT Pub. Date: Nov. 21, 2013

(65) Prior Publication Data
US 2015/0147270 A1      May 28, 2015

Related U.S. Application Data

(60) Provisional application No. 61/649,156, filed on May 18, 2012.

(51) Int. Cl.
A61K 9/00      (2006.01)
A61K 9/50      (2006.01)
(Continued)

(52) U.S. Cl.
CPC .......... *A61K 9/5036* (2013.01); *A61B 5/0071* (2013.01); *A61B 5/4255* (2013.01);
(Continued)

(58) Field of Classification Search
CPC .................................................. A61K 9/5036
See application file for complete search history.

(56) References Cited

U.S. PATENT DOCUMENTS

| | | | |
|---|---|---|---|
| 2007/0053870 A1 | 3/2007 | Tae et al. | |
| 2012/0183621 A1* | 7/2012 | Sinko | A61K 9/5146 424/497 |

(Continued)

FOREIGN PATENT DOCUMENTS

| | | |
|---|---|---|
| WO | WO 2004/096140 | 11/2004 |
| WO | WO 2011/123591 | 10/2011 |

OTHER PUBLICATIONS

Laroui et al. "Drug-Loaded Nanoparticles Targeted to the Colon With Polysaccharide Hydrogel Reduce Colitis in a Mouse Model," Gastroenterology, 2010, vol. 138, pp. 843-853.
(Continued)

*Primary Examiner* — Paul Dickinson
(74) *Attorney, Agent, or Firm* — Occhiuti & Rohlicek LLP

(57) ABSTRACT

The present invention features, inter alia, constructs for the delivery of therapeutic and diagnostic agents to a patient. The constructs can include a nanoparticle, a targeting agent that specifically binds a targeted tissue or cell, a therapeutic moiety, and a hydrogel. The constructs can be used in the treatment and diagnosis of bowel diseases, including inflammatory bowel disease (IBD) and colon cancer. In one embodiment, the therapeutic agent is a nucleic acid that mediates RNA inhibition (RNAi), and the invention is directed to treatments for IBD that combine the positive aspects of such agents {e.g., siRNAs) with the safety of a biodegradable polymeric delivery system to facilitate specific targeting of colonic tissues and cells. As the constructs can be formulated for oral administration, they are well
(Continued)

tolerated and offer advantages with regard to patient compliance.

23 Claims, 1 Drawing Sheet

(51) Int. Cl.
| | |
|---|---|
| *A61K 47/48* | (2006.01) |
| *C12N 15/11* | (2006.01) |
| *A61B 5/00* | (2006.01) |
| *A61K 31/713* | (2006.01) |
| *A61K 39/395* | (2006.01) |
| *A61K 49/00* | (2006.01) |
| *C12N 15/113* | (2010.01) |
| *C12N 15/88* | (2006.01) |

(52) U.S. Cl.
CPC ........ *A61K 31/713* (2013.01); *A61K 39/3955* (2013.01); *A61K 47/482* (2013.01); *A61K 47/48215* (2013.01); *A61K 47/48507* (2013.01); *A61K 47/48915* (2013.01); *A61K 49/00* (2013.01); *C12N 15/111* (2013.01); *C12N 15/1136* (2013.01); *C12N 15/88* (2013.01); *C12N 2310/14* (2013.01); *C12N 2320/32* (2013.01)

(56) References Cited

U.S. PATENT DOCUMENTS

2013/0177598 A1\* 7/2013 Desimone ............... A61K 9/19
424/400
2014/0328897 A1\* 11/2014 Jolck ................... A61K 9/1272
424/450

OTHER PUBLICATIONS

Weng et al. "Targeted Tumor Cell Internationalization and Imaging of Multifunctional Quantum Dot-Conjugated Immunoliposomes in Vitro and in Vivo," Nano Letters, 2008, vol. 8, No. 9, pp. 2851-2857.
Hoshino et al., "Separation of Murine Neutrophils and Macrophages by Thermoresponsive Magnetic Nanoparticles," *Biotechnology Progress*, 23(6):1513-1516, 2007.
Laroui et al., "Nanomedicine in GI," *Am. J. Physiol. Gastrointest. Liver Physiol.*, 300(3):G371-G383, 2010.
Laroui et al., "Functional TNFα Gene Silencing Mediated by Polyethyleneimine/TNFα siRNA Nanocomplexes in Inflamed Colon," *Biomaterials*, 32(4):1218-1228, 2011.
Laroui et al., "Designing Targeted F4/80-Coated TNFA SiRNA-Loaded Nanoparticles: A Novel Therapeutic Approach to Treat IBD," Database accession No. PREV201200606059, Database Biosis [online] Biosciences Information Service, Philadelphia, PA, USA, Meeting Abstract, Digestive Disease Week, San Diego, CA, USA, May 19-22, 2012.

\* cited by examiner

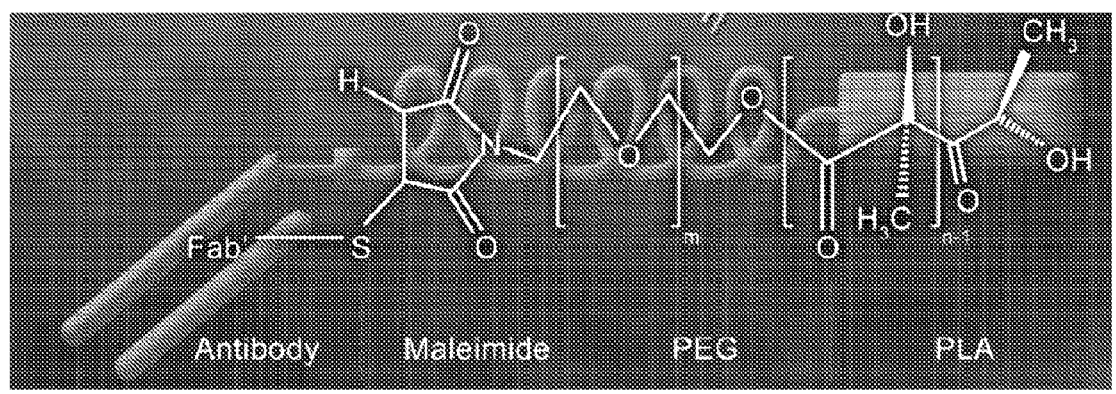

CONSTRUCTS FOR DIAGNOSING AND TREATING INFLAMMATORY BOWEL DISEASES AND COLON CANCER

CROSS-REFERENCE TO RELATED APPLICATIONS

This application is a U.S. national phase application of International Application No. PCT/US2013/041741, filed May 18, 2013, which claims the benefit of the filing date of U.S. Provisional Application No. 61/649,156, which was filed May 18, 2012. The content of the earlier-filed applications is hereby incorporated by reference herein in its entirety.

STATEMENT CONCERNING FEDERALLY SPONSORED RESEARCH

This invention was made with government support under grant numbers K01-DK-097192 and RO1-DK-071594 awarded by the National Institutes of Health. The government has certain rights in the invention.

BACKGROUND

Inflammatory bowel disease (IBD), which includes Crohn's disease and ulcerative colitis, is a relapsing and remitting chronic disease for which treatment options are limited. Further, most existing treatments are associated with significant side effects. Newer, targeted treatments such as treatment with anti-tumor necrosis factor (anti-TNF) agents are effective in a subset of patients but these treatments are administered systemically and are also associated with significant side effects. The ability to target drugs to the site of inflammation in sufficient quantities to maximize local drug concentration and minimize systemic side effects would represent a major advance in therapeutic strategies for treating diseases such as IBD. Targeting drugs to the site of inflammation has remained a challenge in IBD because of the lack of vehicles that can carry sufficient drugs or that can release the drugs they carry at the site of inflammation. It is also challenging to deliver drugs to the gastrointestinal (GI) tract, particularly the colon, due to degradation by digestive enzymes. Various carriers have been designed to release the drug at a specific pH value, to be resistant to digestive enzymes, and/or to require bacterial cleavage for activation, and several of these types of carriers are currently being investigated. However, most delivery systems under development still require the initial incorporation and/or administration of drugs in large doses, multiple times a day, resulting in poor patient compliance.

SUMMARY OF THE INVENTION

The present invention features delivery vehicles that include nanoparticles (NPs) that may be biodegradable and have little or no associated toxicity. Among other uses, these vehicles can be used to target TNFα with siRNAs for treatment of bowel diseases such as colitis and colon cancer.

While the present delivery vehicles are not limited to those that achieve their effects by any particular physiological mechanism, we believe that grafting or linking a targeting agent to a NP improves the kinetics of endocytosis as well as the ability of the NP to target a given cell (e.g., a macrophage or cancer cell). Nanoparticles can enter cellular targets by endocytosis. The resulting endosome is degraded, allowing release of the double-stranded RNAs delivered by the present constructs and their incorporation into the RISC. Targeting ability can be assessed by flow cytometry and other methods known in the art, and we use the term "target" as it is generally understood in the art to mean the selective delivery of an agent to an identified cellular or molecular entity to the substantial exclusion of others. For example, the delivery vehicles of the present invention can target colonic macrophages or dendritic cells by selectively delivering a therapeutic or diagnostic moiety to those cells, to the substantial exclusion of others. Among the other advantages of the present delivery vehicles may be an ability to directly release specific siRNAs to target cells. The NPs are readily able to pass through physiological barriers and evade phagocytosis. They also can show rapid mixing kinetics, accept high loading concentrations, confer little or no toxicity, and resist degradation.

BRIEF DESCRIPTION OF THE DRAWING

FIG. 1 is a schematic illustration of a therapeutic agent linked via a functionalized maleimide linker to a nanoparticle, as described herein with the present constructs.

DETAILED DESCRIPTION

The present invention features, inter alia, a versatile delivery system for therapeutic and diagnostic agents that can overcome physiological barriers and target inflamed or cancerous regions of the colon. Using the delivery vehicles, one can administer less of a given therapeutic or diagnostic agent (than would be required without the delivery vehicle) but achieve similar therapeutic efficacy or diagnostic success. In some embodiments, about a hundred- or even a thousand-fold less of a given agent can be administered efficaciously when delivered via the present constructs. Thus, in one aspect, the invention features delivery vehicles that include (a) at least one nanoparticle (NP) and preferably a plurality of NPs, (b) a targeting agent that binds (e.g., specifically binds) a targeted tissue or cell, and (c) a hydrogel. We may use the terms "vehicle" and "construct" interchangeably. The vehicle or construct is assembled such that the targeting agent is associated with the nanoparticle, thereby forming a core structure, and the hydrogel is generally peripheral to the core; the hydrogel fully or substantially encapsulates the core structures. While there may be areas of integration and overlap between a given core structure and the hydrogel, and while there may be some areas in which the hydrogel does not completely encapsulate each and every core structure, the hydrogel is generally positioned peripheral to the core structures. The targeting agent can be directly associated with the nanoparticle by covalent or non-covalent bonds or it may be indirectly associated with the nanoparticle by way of a linker.

As the constructs are designed for the delivery of therapeutic moieties (to effect treatment of bowel disease) or detectable markers or imaging agents (to facilitate diagnosis of bowel disease), the constructs can further include a therapeutic moiety, a detectable marker, and/or an imaging agent. In some instances, a single agent may have both therapeutic and diagnostic capabilities. Where a therapeutic moiety, diagnostic marker, and/or imaging agent is also a part of the construct, the therapeutic moiety, diagnostic marker, and/or imaging agent can be directly or indirectly associated with the nanoparticle by covalent or non-covalent bonds. For example, the targeting agent can be associated with a nanoparticle by way of covalent bonds through a linker, such as the functionalized maleimide-PEG linker described below, and the therapeutic agent (e.g., an siRNA as described further below) or diagnostic agent can be non-covalently bound directly to the nanoparticle through electrostatic force.

Maleimide is well known in the art as a chemical compound with the formula $H_2C_2(CO)_2NH$. It is an unsaturated imide, and the term "maleimides" also describes a class of derivatives of the parent maleimide where the NH group is replaced with alkyl or aryl groups such as a methyl or phenyl, respectively. Maleimide and these derivatives are useful in the linkers of the present invention, which can reside between a targeting agent and an NP. The substitution or substituent can also be a polymer such as polyethylene glycol or another polymer as described herein. Maleimide and derivatives thereof can be prepared from maleic anhydride by treatment with amines followed by dehydration. Maleimides linked to polyethylene glycol chains are known in the art and are useful in the context of the present constructs as a linker.

In the constructs, the nanoparticles can have a varied diameter, preferably in the range of about 1-1,000 nm. For example, the nanoparticles can range in diameter from about 1-10 nm, and such NPs can be formed by crystalline iron atoms or micelles of small molecules. Other useful size ranges include about: 1-100 nm; 100-250 nm; 1-250 nm; 1-400 nm; 100-400 nm; 100-500 nm; 250-500 nm (e.g., about 375 nm); 400-500 nm; 500-750 nm; 500-1000 nm; 1-750 nm; 750-1000 nm; and ranges within and between these. About 100-400 nm may be preferred. The NPs within a given construct or vehicle may be essentially or roughly of the same size, or they may vary in size. NPs of about 10-1000 nm are typically generated from polymeric materials, and any such NPs are useful in the context of the present invention. The NPs can include more than one type of polymer and can include co-polymers. As demonstrated in the Examples below, the NP can be fashioned from PLA-PEG. One of ordinary skill in the art will recognize that the resulting size depends on the synthetic process used to prepare the NPs, and such methods are known in the art. For example, NPs useful in the present constructs can be formed by applying energy to fragment the bulk materials or by the nucleation and growth of seeds through chemical processes. Although there is variability in the size of the NPs that can be used, in general, the NPs should be considerably smaller than the size of the cells with which they will interact (i.e., of a target cell). Nonphagocytic eukaryotic cells can internalize particles less than about 1 μm in size. NPs having a diameter of about 5-110 nm are understood to be in development as potential carriers of anticancer drugs via intracellular drug delivery. Although the invention is not limited to constructs that achieve delivery of therapeutic and/or diagnostic agents by any particular mechanism, NPs that are less than about 200 nm in size are thought to be taken up by the epithelium mainly in the intestinal epithelial cells on villi tips or by the M cells. We use the term "about" to indicate variability of a given parameter (e.g., here, the diameter of the NPs) within 10% of the value specified. For example, a NP having a diameter of about 500 nm has a diameter in the range of 450-550 nm.

The NPs can have an electrostatic surface charge. Zeta potential approximates the charge on a NP and is used to describe cell-nanomaterial (NM) interactions. Higher zeta (positive or negative) can produce a stronger electrostatic repulsion between NMs, and NM suspension will likely be more stable as a result. Charge depends on the polymer used for the NM matrix or can be modulated by adsorbing specific molecules onto the NM surface.

The NPs used herein can be (and generally are) spherical. The NPs used herein can be micelles, liposomes or lipid NPs, many of which have been well characterized. The NPs can have a surface area-to-volume ratio of 3/r. As r decreases, the surface area-to-volume ratio increases. A particle with a larger surface area has more interaction sites available and the rate of an interaction at the surface may be higher. Useful liposomes can be synthesized with a mixture of lipids with different surface charges (cationic, neutral, and anionic). More specifically, NPs within the present constructs can be cationic liposomes such as DOTAP, DOTMA (lipofectin) and DOSPA (lipofectamine). Generally, these liposomes easily interact with negatively charged siRNA via electrostatic interaction. Any of the incorporated NPs can include polyethylene glycol, as described by Gomes-da-Silva et al.

The constructs or vehicles of the present invention can include NPs formed (exclusively or partially) from naturally occurring polymers (e.g., a protein or polysaccharide). Numerous polysaccharides are known in the art to be amenable to formation of NPs, and any of these can be used in the present vehicles. For example, the polysaccharide can be alginate, chitosan, pectin, amylopectin, or a mixture of any two of more of these polysaccharides. Other useful natural polymers include proteins such as gelatin and albumin. Alternatively, or in addition, the NPs can be formed from synthetic polymers (e.g., poly(meth-)acrylate or polyacrylamide).

The materials of the present vehicles, including the NPs therein, can be biodegradable or non-biodegradable. Suitable biodegradable polymers include polyorthoesters, polyanhydrides, polyamides, polyalkylcyanoacrylates, polyesters, lactides and/or glycolides, polycaprolactones, polyphosphazenes, and pseudo-polyamino acids. Suitable non-biodegradable polymers include silicone, an elastomer, polyethylene oxide, polyethylene glycol, or an acrylic polymer. Suitable aliphatic polyesters include poly(D,L-lactide) and poly(glycolide) and co-polymers thereof. In other studies, a mixture of two polysaccharides (alginate and chitosan) produced a high drug release profile from the NPs in the targeted area. The kinetics of the release can be modulated by the osmotic activity of the salt or charged polymers, and/or the erosion rate of the polymer coating. Eudragit poly(meth-)acrylate polymers can also be used, as can polymers containing acidic or alkaline groups that enable the pH-dependent release of the therapeutic moiety or detectable agent. Polyacrylamide is a polymer that is highly sensitive to pH. It is stable in acidic pH but degraded in a neutral pH. This characteristic is suitable for drug protection during GI tract transit. The polymer can be water-insoluble; the polymer can be ethyl cellulose; the polymer can be amylase/amylopectin; and polymers can be bonded via noncovalent or covalent interactions directly during the NP synthesis or after synthesis by surface modification reactions. Covalent linkages based on carbonyl, amine, or silane coupling chemistries allow a wide range of functionalities under various pH or oxidative conditions. Amide, ester, disulfide, hydrazone, or thioether linkages have been used to enable covalent or hydrophobic interactions (hydrophobic drug loading) or ionic interactions (nucleic acids) and are useful in the present invention. Hydrophobic, electrostatic, or hydrogen-bonding interactions present alternatives to covalent linkages, particularly if flexibility under chemical conditions is required. In some embodiments, the present constructs employ maleimide/thiol group-mediated covalent bonding. For example, NPs (e.g., comprising PLA-PEG) can be grafted to a targeting moiety (e.g., an antibody) via maleimide/thiol group-mediated covalent bonding. Our studies to date indicate this improves the macrophage (MP)-targeting kinetics of the NPs to cells at least in vitro.

The NPs can be particulate dispersions or solid particles in which a therapeutic moiety (or "drug") and/or a diagnostic or imaging agent can be dissolved, entrapped, or attached.

The therapeutic moiety can be any moiety known or determined to be useful in treating IBD, including Crohn's disease and colitis (e.g., ulcerative colitis), IBS (irritable bowel syndrome), or colon cancer. Patients with IBD show defects in intestinal epithelial barrier function that can allow bacteria to colonize the colonic epithelia (Gassler et al., *Am. J. Physiol.* 281: G216-228, 2001; Tummala et al., *Curr. Opin. Gastroenterol.* 20:592-597, 2004). Bacterial antigens are presented to dendritic cells and macrophages, which secrete pro-inflammatory cytokines to the lamina propria, triggering recruitment of circulating immune cells via the expression of adhesion molecules on endothelial and immune cells (Cucchiara et al., *J. Clin. Gastroenterol.* 46:S64-S66, 2012). These pathogenic processes are the targets of modern research on therapeutic approaches for IBD, which include the development of inhibitors of inflammatory cytokines (e.g., anti-TNFα) that induce T-lymphocyte apoptosis, the identification of anti-inflammatory cytokines that downregulate T-lymphocyte proliferation, and the synthesis of selective adhesion molecule (SAM) inhibitors that suppress the trafficking of T-lymphocytes into the gut epithelium (see Rutgeerts et al., *Alimentary Pharmacol. & Therapeutics* 17:1435-1450, 2003; Scallon et al., *Cytokine* 7:251-259, 1995; Hanauer et al., *Lancet*, 359:1541-1549, 2002; Tchilian et al., *Immunology* 92:321-327, 1997; Nielsen et al., *Digestive Diseases and Sciences*, 39:1918-1923, 1994; Jones et al., *Gut* 36:724-730, 1995; Pooley et al., *Digestive Diseases and Sciences*, 40:219-225, 1995; Burns et al., *Gastroenterol.* 121:1428-1436, 2001; Taniguchi et al., *J. Gastroenterol. and Hepatol.* 13:945-949, 1998; Hamamoto et al., *Clinical and Experimental Immunol.* 117: 462-468, 1999; Bennett et al., *J. Pharmacol. and Exp. Ther.* 280:988-1000, 1997). For example, the therapeutic moiety can be an anti-inflammatory peptide (e.g., the tripeptide KPV); dexamethasone; the anti-inflammatory molecule 5-amino salicylic acid; insulin; or an inhibitor of an inflammatory cytokine.

The invention encompasses pharmaceutical and physiologically acceptable compositions for administration to a patient, and these compositions can be formulated for oral or parenteral administration. For ease and better patient compliance, oral formulations are preferred. Such compositions can be generated using information readily available in the pharmaceutical arts to produce pills, pellets, capsules, tablets, lozenges, syrups, suspensions, and the like for oral administration. The formulations may include mechanisms allowing for delayed or sustained release.

The constructs of the invention can include therapeutic moieties and/or diagnostic agents of a variety of types, including polypeptides, nucleic acids, radioisotopes, and metals suitable for photodynamic therapy. The polypeptide can be a peptide consisting of 3-10 amino acid residues. Where the moiety or agent is a nucleic acid, it can be one that mediates RNA interference (RNAi; e.g., an siRNA, shRNA, oligonucleotide, antisense RNA, or microRNA). Nucleic acids useful in the present drug delivery vehicles include those that inhibit an inflammatory cytokine (e.g., TNFα or another cytokine that induces T-lymphocyte apoptosis) or a selective adhesion molecule (SAM) that suppresses the trafficking of T-lymphocytes into the gut epithelium. In a specific embodiment, where the therapeutic moiety is a nucleic acid that inhibits TNFα, one can employ the sense strand CGUCGUAGCAAACCACCAATT (SEQ ID NO: 1) and the antisense strand UUGGUGGUUUGCUAC-GACGTG (SEQ ID NO:2). One of ordinary skill in the art can select and design other inhibitory nucleic acids (e.g., nucleic acids directed to other portions or the TNFα RNA sequence) based on sequence-specific information readily known in the art. Alternatively, or in addition to using a nucleic acid that mediates RNA interference, the present drug delivery vehicles can include a nucleic acid that, when delivered to a target cell, is expressed as a therapeutic protein. For example, one can deliver nucleic acids encoding the tripeptide Lys-Pro-Val or an anti-inflammatory cytokine that downregulates T-lymphocyte proliferation.

The therapeutic moiety or agent can also be a small organic molecule or, more generally, a non-protein, non-nucleotide chemical compound. For example, one can incorporate, as the chemical compound, an anti-inflammatory agent (e.g., an agent that inhibits the expression or activity of an inflammatory cytokine such as tumor necrosis factor alpha (TNFα)). The therapeutic moiety can be associated with the nanoparticles by virtue of being dissolved, entrapped, or attached thereto, and any vehicle that includes a therapeutic moiety can also include a detectable label or tag or facilitate visualization or detection in a target tissue. The therapeutic moieties can be associated with the nanoparticles by complexation with a complexing agent (e.g., polyethylenimine, chitosan, poly-L-lysine, or a cationic polymer).

The targeting agent that binds (e.g., specifically binds) a target tissue (e.g., a human cell or tissue) can be an antibody or a fragment or other variant thereof that binds the target tissue (e.g., an scFv). Although the invention is not so limited, when a TNF receptor is targeted, the antibody moiety can be adalimumab, certolizumab pegol, golimumab, or infliximab, an scFv comprising the variable regions of the heavy and light chains of adalimumab, certolizumab pegol, golimumab, or infliximab, or a biologically active variant of these tetrameric or single chain antibodies. For example, the antibody moiety can be an Fab or F(ab')2 fragment of adalimumab, certolizumab pegol, golimumab, or infliximab. With respect to antibody targeting agents, the targeting agent can be a tetrameric antibody, a biologically active variant thereof, an scFv, Fab fragment, Fab' fragment, or F(ab')2 fragment, or a biologically active variant thereof, regardless of class (i.e., whether of the IgG class or another class) and whether human, humanized, chimeric, polyclonal, monoclonal, or having any other attribute or characteristic described herein).

The targeting agent can also be a ligand or a peptide ligand mimetic. If desired, any combination of such agents can also be employed. A goal of active targeting is to facilitate nanoparticle accumulation in close proximity to a target cell or tissue and to permit active crossing of the cell membrane by therapeutic materials. This can facilitate, for example, siRNA transport into the cytoplasm to activate RNAi pathways. In the Example below, the targeting agent is an F4/80 antibody, which targets nanoparticles bearing TNFα siRNA to macrophages in the mouse. Thus, the targeting agent incorporated in the present constructs can be a macrophage-specific ligand or receptor. More generally, the targeting agent can be a receptor, a receptor ligand, a chemoattractant agent, an extracellular matrix protein, or an antibody or biologically active variant or other fragment thereof that specifically binds a target tissue or cell affected by a bowel disease or gastrointestinal cancer.

In any of the constructs or vehicles of the invention, the targeting agent can include a protein or peptide (both amino acid polymers; the term "protein" being generally applied for longer polymers and/or "full-length" naturally occurring proteins and the term "peptide" or "polypeptide generally being applied to describe shorter polymers or fragments of full-length, naturally occurring proteins). The targeting agent can bind a cell or tissue within the gastrointestinal tract, and that cell or tissue may be cancerous.

Where the targeting agent is a receptor, it can be an integrin (e.g., integrin β2) or an active fragment or other variant thereof. Generally, biologically active fragments and other variants of naturally occurring targeting agents are useful in the present vehicles so long as they retain the ability to bind (e.g., specifically bind) a target cell or tissue of interest (e.g., a macrophage or colon cancer cell). The targeting agent (e.g., an antibody) can also target (e.g., specifically bind) an extracellular matrix protein or integrin. As targeting agents, useful antibodies to integrins include the humanized antibodies efalizumab (Raptiva®) and natalizumab (Tysabri®), which have been used for the treatment of autoimmune diseases and are being evaluated for treatment of IBD. In this way, antibodies "targeting" leucocyte integrins can be used not only to target nanoparticles to leucocytes but also to serve as a treatment along with therapeutic agents such as siRNAs targeting TNFα. In the Examples below, we describe the use of an integrin β2-coated TNFα-siRNA-loaded delivery vehicle in a murine model of colitis.

In any embodiment, the targeted tissue can be a human tissue (e.g., a human macrophage). In any embodiment, the targeting agent and/or the therapeutic moiety can be grafted to the nanoparticle via a polymeric spacer (e.g., a polymeric spacer comprising a functionalized maleimide such as maleimide-polyethyleneglycol-poly(lactic acid)). In any embodiment, the targeting agent can be integrin β2; the therapeutic agent can inhibit the expression or activity of TNFα; and/or the hydrogel can include alginic acid and/or chitosan. In any embodiment, the vehicle can be formulated for oral administration, and the formulation can include a physiologically acceptable excipient (many of which are known and used in the art).

The formulations (i.e. physiologically or pharmaceutically acceptable formulations for administration to a patient) can be configured to include low doses of the therapeutic agents; "low" being relative to the amount required in the absence of the delivery vehicle. Thus, the present constructs can be formulated to deliver a lower dose of the therapeutic agent relative to the amount required in the absence of the delivery vehicle, the lower dose nevertheless being an effective dose. In terms of absolute dosages, one of ordinary skill in the art will recognize that the amount required will vary depending on the nature and severity of the condition to be treated, the age, sex, and weight of the patient to be treated, and similar considerations. RNA molecules that mediate RNA inhibition may be delivered in the range of about 10-200 μg kg$^{-1}$ (about 25, 50, 60, 70 80, 100, or 150 μg kg$^{-1}$).

A variety of hydrogels can be used to encapsulate or surround (fully or partially) the core components of the present vehicles. For example, one can employ a hydrogel including alginic acid and/or chitosan. For example, a NP described herein, decorated to constitute a core structure, can be encapsulated in an alginate-chitosan hydrogel as described by Laroui et al., (*Gastroenterol.* 138:843-853 e841-842, 2010). See also Laroui et al., *Nature Protocol Exchange doi:* 10.1038/nprot.2009.165.

The methods of the invention include methods of treating a patient who is suffering from an inflammatory bowel disease or colon cancer. The methods can be carried out by administering to the patient a drug delivery vehicle as described herein, and any of the methods can include the step of identifying a patient in need of treatment. The patient can be a human or a domesticated animal such as a cat, dog, or horse.

In another aspect, the invention encompasses the use of the drug delivery vehicles described herein in the preparation of a medicament. The medicament can be intended for the treatment of irritable bowel syndrome, inflammatory bowel disease (e.g. Crohn's disease or ulcerative colitis) or colon cancer.

In another aspect, the invention encompasses diagnostic vehicles that include a plurality of nanoparticles, a targeting agent that specifically binds colon cancer cells, a detectable moiety, and a hydrogel. The targeting agent and the detectable moiety are associated with the nanoparticles, thereby forming a core, and the hydrogel is generally peripheral to the core. In vehicles having a diagnostic component, the detectable moiety can be an agent that can be visualized or detected by instrumentation. For example, the detectable moiety can be a fluorophore, radioisotope, metal, or photo-sensitive molecule.

The methods of the invention also includes methods of diagnosing a patient. For example, the invention features methods of diagnosing colon cancer by administering to a patient a diagnostic vehicle as described herein in which the targeting agent binds (e.g., specifically binds) colon cancer cells; and exposing the detectable moiety to a detection signal. Retention of the detectable moiety within the colon indicates the presence of colon cancer cells in the patient. Any of the diagnostic methods can include a step of identifying a patient at risk for developing colon cancer.

In another aspect, the invention encompasses the use of the diagnostic vehicles described herein in the preparation of a medicament. The medicament can be intended for the diagnosis of or the detection of colon cancer.

In another aspect, the invention features a kit including a drug delivery vehicle or a diagnostic vehicle as described herein and instructions for use.

In another aspect, the invention features methods of synthesizing NPs and delivery vehicles as described herein. The methods can include a step of providing a nanoparticle; a step of conjugating the nanoparticle, optionally through a linker to a targeting agent; a step of conjugating the nanoparticle to a therapeutic agent, an imaging agent, or a detectable marker; and a step of encapsulating the conjugated nanoparticle (the core structure) in a hydrogel. NPs can be obtained from a commercial supplier or synthesized by methods known in the art (e.g., the double emulsion/solvent evaporation method described by van den Berg and Kraal (*Trends in Immunol.* 26:506-509, 2005).

The efficacy of any given drug delivery vehicle can be tested in in vivo models of GI disease and/or in clinical trials by assessing any number of signs and symptoms associated with the disease (e.g., weight loss, myeloperoxidase activity, and Iκbα accumulation, all of which should be attenuated relative to untreated subjects or to subjects treated with the therapeutic moiety delivered independently of the present drug delivery vehicles.

With regard to the present invention and the specificity of this description, various components and steps have been described. It is to be understood that any one or more of these components or steps can be explicitly excluded from a construct, formulation, kit, method, or the like, as described herein. For example, the description specifies that the drug delivery vehicles can include NPs comprising the polysaccharide alginate, chitosan, or pectin. It is to be understood that the NPs can therefore include alginate and chitosan but not pectin; alginate and pectin but not chitosan; alginate but not chitosan or pectin; and so forth.

As noted, TNF-α plays a crucial role as the central pro-inflammatory mediator in the pathogenesis of IBD, and patients have been successfully treated with anti-TNF-α antibodies in multiple clinical trials (de Vries et al., *Clinical and Experimental Allergy* 39:731-739, 2009; Holtmann and Neurath, *Int'l. J. Colorectal Disease* 20:1-8, 2005; and Myers et al., *J. Pharmacol. And Exp. Therapeutics* 304:411-424, 2003). Such antibodies have been demonstrated to reduce intestinal inflammation in patients and in various animal models, including DSS-induced colitis in mice, and these antibodies or biologically active variants thereof can be incorporated into the drug delivery vehicles described herein (see de Vries et al., *Clinical and Experimental Allergy* 39:731-739, 2009; Filleur et al., *Cancer Res.* 63:3919-3922, 2003; Peer et al., *Proc. Natl. Acad. Sci. USA* 104:4095-4100, 2007). However, nearly 25% of patients taking the monoclonal antibody, infliximab, experienced at least one serious adverse effect, such as pneumonia, cancer, or acute inflammation (Holtmann and Neurath, *Intl. J. Colorectal Disease* 20:1-8, 2005; 8, 2005; and Tillack et al., *Gut*, 2013). The observed adverse effects are believed to be due primarily to the lack of targeted administration and the drug "over dosage" usually inherent to systemic drug administration. Furthermore, the mechanism(s) by which antibodies against TNF-α function remain poorly understood (Kojoharoff et al., *Clin. Exp. Immunol.* 107:353-358, 1997). In other studies, high-dose systemic administration of TNF-α antisense oligonucleotides to mice was found to ameliorate acute and chronic colitis in both DSS-treated and IL-10-deficient mice (Myers et al., *J. Pharmacol. And Exp. Therapeutics* 304: 411-424, 2003). The intravenous injection of these siRNA formulations required doses ranging from 50 to 125 mg kg$^{-1}$ in mice (Filleur et al., *Cancer Res.* 63:3919-3922, 2003; Peer et al., *Proc. Natl. Acad. Sci. USA* 104:4095-4100, 2007; McCaffrey et al., *Nature* 418:38-39, 2002; Song et al., *Nature Biotechnol.* 23:709-717, 2005; Soutschek et al., *Nature* 432:173-178, 2004; Wesche-Soldato et al., *Blood* 106:2295-2301, 2005) and 1 mg kg$^{-1}$ in nonhuman primates (Zimmermann et al., *Nature* 441:111-114, 2006). In the studies described below, we demonstrated that the effective dose can be significantly decreased by NP-mediated targeting and increased cellular uptake. Our experiments revealed that 60 μg kg$^{-1}$ TNF-α siRNA could silence TNF-α expression by 60% in intestinal MPs of NP-treated mice in vivo. We also demonstrated that ~30% of the intestinal MPs were able to take up the NP-delivered TNF-α siRNA.

The high potency of such low doses of TNF-α siRNA is likely to result from the PEI-mediated protection of siRNAs against nuclease and the proton sponge effect associated with such PEI complexes (Laroui et al., *Biomaterials* 32:1218-1228, 2011; Bolcato-Bellemin et al., *Proc. Natl. Acad. Sci. USA* 104:16050-16055, 2007; and Hobel and Aigner, *Methods in Mol. Biol.* 623:283-297, 2010). In addition, coating the TNF-α siRNA-loaded NPs with the Fab' fragment of the F4/80 Ab increased the specificity of their binding to intestinal MPs. Colitis is characterized by stricture (a narrowing of the intestinal wall), perforation, hemorrhage, abscesses, fistula and diarrhea, meaning that fast drug uptake is required for efficient and optimal dosing. This requirement influenced our strategy of NP design, and our results emphasize the beneficial effect of the antibody fragment we tested on the kinetics of uptake and the recognition of NPs by MPs. We demonstrate that oral administration of our MP-homing, siRNA-engineered vehicle can lead to the direct release of TNF-α siRNA in intestinal MPs, reducing colitis in a mouse model.

EXAMPLES

Example 1

An F4/80-Coated TNFα siRNA-Loaded Nanoparticle

Two copolymer types were synthesized: maleimide-polyethyleneglycol-poly(lactic acid) and methoxypolyethyleneglycol-poly(lactic acid). Use of the first polymer permitted grafting of a mouse F4/80 antibody directly onto NPs, employing the functionality of maleimide, and the second polymer served in construction of an antibody-free control (a naked NP). Copolymer synthesis employed ring-opening polymerization in dry toluene under a moisture-free atmosphere of high-purity argon. The two copolymers were analyzed using H1NMR. The integrity of antibody grafted onto NPs was assessed by measurement of the interaction force between cells expressing F4/80 (Raw 264.7) and cells negative for F4/80 receptor expression (Caco2 BBE cells) using a Surface Plasmon Resonance (SPR) biosensor instrument.

Knowing the final concentration of F4/80 after reaction with the NPs and the average diameter of NPs measured by light scattering (375 nm), we determined that the average number of F4/80 antibodies per NP was 2,073. We determined the binding characteristics of F4/80 receptors (expressed on macrophages) to the F4/80 antibody ligand bound to NPs (coated onto the surface of a gold chip). We found that Raw 264.7 (binding coefficient ~50) but not Caco2 BBE cells (binding coefficient ~0.5) bound to the chip coated with NPs covered with F4/80 antibody. In addition, we found that FITC-containing NPs targeted using the F4/80 antibody were taken up by Raw 264.7 cells but not by Caco2 BBE cells after 15 minutes of incubation.

Our study offers proof of principle that NPs can be used as a novel therapeutic modality facilitating targeted site and cell type-specific drug delivery for treatment of IBD. We expect such a system to be associated with minimal side effects.

Example 2 siRNA Anti-TNFα-Loaded Nanoparticles that Target Colonic Macrophages Offer an Effective Therapy for Experimental Colitis In the study described below, we demonstrate that a therapeutic agent—an siRNA that targets TNFα—can be efficiently loaded into nanoparticles (NPs) made of PLA-PEG and that grafting of the targeting agent—an Fab' portion of the F4/80 Ab—onto the NP surface via maleimide/thiol group-mediated covalent bonding improves the macrophage (MP)-targeting kinetics of the NPs to RAW264.7 cells in vitro. We observed direct binding between MPs and the antibody-bearing NPs. Next, we orally administered hydrogel (chitosan/alginate)-encapsulated antibody-bearing NPs loaded with TNFα siRNA to mice treated with 3% dextran sodium sulfate (DSS) and investigated the therapeutic effect on colitis. In vivo, the release of TNFα-siRNA-loaded NPs into the mouse colon attenuated colitis more strongly when the NPs were covered with the Fab' portion of the F4/80 Ab, compared to uncovered/untargeted NPs. All DSS-induced parameters of colonic inflammation (e.g., weight loss, myeloperoxidase activity, and IκbαIk accumulation) were attenuated. Grafting the Fab' part of the F4/80 Ab onto the NPs improved the kinetics of endocytosis as well as the MP-targeting ability, as indicated by flow cytometry. Collectively, our results show that PLA-PEG NPs covered with the Fab' fragment of the F4/80 Ab are powerful and efficient nanosized tools for delivering siRNAs into colonic macrophages.

Our optimized NP synthesis process allows encapsulation of many types of water-soluble molecules, including the prohibitin protein (Theiss et al., *Inflamm. Bowel Dis.* 17:1163-1176, 2011) and siRNAs. As is now well appreciated, the discovery of siRNA by Fire and Mello (see Fire et al., *Nature* 391:806-811, 1998) introduced an innovative approach to the field of gene therapy, allowing single target genes to be turned off without genomic integration of exogenous DNA. The delivery of siRNA to target tissues via traditional agents (e.g., Lipofectamine™) have proven challenging because naked siRNA lacks stability and shows poor pharmacokinetics (Pecot et al., *Nature Reviews, Cancer* 11:59-67, 2011; Whitehead et al., *Nature Reviews, Drug discovery* 8:129-138, 2009; Mohanan et al., *J. Controlled Release* 147:342-349, 2010), but pre-complexation with polyethyleneimine (PEI) has been shown to protect against degradation, enhance drug loading, and increase siRNA efficiency via the "proton sponge effect" (Laroui et al., *Biomaterials* 32:1218-1228, 2011; and Laroui et al., *Methods in Enzymology* 509:101-125, 2012).

Specifically, we orally administered intestinal-MP-targeting encapsulated F4/80 antibody-coated TNFα-siRNA-loaded NPs and examined colitis in a mouse model using the following methods, which are applicable to the compositions and methods of the invention. Preparation of TNFα siRNA/PEI loaded NPs: NPs were synthesized via double emulsion/solvent evaporation, as described previously (van den Berg and Kraal, *Trends in Immunol.* 26:506-509, 2005. Briefly, an internal phase (see details below) containing the drug was mixed with 20 g/L of PLA-PEG or PLA-PEG-Mal in dichloromethane to generate a water-in-oil (W/O) emulsion after 2 minutes of vortexing (Maxi Mix II, Thermodyne, Dubuque, Iowa) and 1 minute of sonication with 50% active cycles at 70% power (Pmax=400 W) (Digital Sonifier 450, Branson, Danbury, Conn.). This first emulsion was dropped in a second water phase containing 0.3 g/L of PVA to generate a water/oil/water (W/O/W) emulsion. The W/O/W emulsion was dropped in a dispersing phase of 0.1 g/L polyvinylic alcohol (PVA) and stirred at 45° C. under a vacuum to remove dichloromethane. NPs were centrifuged at 9953 g and freeze-dried overnight at −50° C. under 0.1 mbar pressure. As the second emulsion allowed PVA to be grafted on the surface by hydrophobic interaction with the PLA matrix, NPs were coated with PVA to prevent aggregation through electrostatic repulsions.

Preparation of the internal phase: The internal phase has a typical N/P ratio of the number of negative charges of siRNA (TNFα siRNA or FITC-tagged siRNA) (P as the phosphorous charge) and positive charges of PEI (N as the ammonium charge) (N/P ratios of 30 for PEI). A mixture of siRNA/PEI:29 μL TNFα siRNA (5 μM) was combined with 18 μL PEI (5 mM), and incubated for 10 minutes at room temperature for complexation. After 10 minutes, a polyplex was formed, and 750 μL bovine serum albumin (BSA, 50 g/L) was added, generating the first emulsion with dichloromethane.

Synthesis of Fab' portion of the F4/80 antibody: The F4/80 Ab is first digested by pepsin to remove the Fc part involved in complement recognition and the MPs binding on the whole antibody. Pepsin, a nonspecific endopeptidase, is used to enzymatically digest the Fc portion of whole IgG to yield the fragment known as F(ab')$_2$. This fragment is composed of a pair of Fab' units connected by two disulfide bonds. As the pepsin protease is supplied in immobilized form as beaded agarose resin, the digestion reaction is stopped by removing the resin from the IgG solution; the result is digest products that are enzyme-free. In order to link the Fab' portion of the F4/80 Ab to the maleimide linker extending from the NP matrix, —SH functional groups were generated by mild reduction using 2-Mercaptoethanol (Thermo Scientific Pierce, Pittsburgh, Pa.) to cleave Fab disulfide bonds. The final result was an Fab' fragment of the F4/80 antibody which could be "plugged into" the NPs surface presenting functionalized maleimide.

Cell Culture: RAW 264.7 cells (mouse MPs) were cultured to confluence in 75-cm$^2$ flasks at 37° C. in a humidified atmosphere containing 5% (v/v) $CO_2$. The culture medium was DMEM/Ham's F-12 medium (Invitrogen, Grand Island, N.Y.) supplemented with 1-glutamine (2 mM), penicillin (100 units/ml), streptomycin (100 μg/ml), and heat-inactivated fetal calf serum (10%, v/v) (Atlanta Biologicals, Atlanta, Ga.). For the fluorescent study, we placed a plate checker in the incubator (15 minutes, 200 Hz).

WST-1: To assess the potential toxicity of NPs before (NP PEG-PLA-Mal) or after (NP PEG-PLA-Ab) conjugation with the Fab' fragment, a WST-1 assay was performed. As described previously, RAW 264.7 cells were seeded in 96-well plates at a density of $5 \times 10^4$ cells per well and exposed to 1 mg/mL of empty NPs (NP PEG-PLA-Ab empty), empty non Fab'-covered NPs (NP PEG-PLA-Mal) and TNFα siRNA loaded NPs including the Fab' fragment as a targeting agent (NP PEG-PLA-Ab with TNFα siRNA) for 48 hours. The WST-1 assay measures cleavage of the soluble red tetrazolium salt, WST-1 (4-[3-(4-iodophenyl)-2-(4-nitrophenyl)-2H-5-tetrazolio]-1,3-benzene disulfonate), by dehydrogenase present in intact mitochondria, which leads to the formation of dark red formazan crystals. WST-1 proliferation reagent (10 μL) was added to cells (10 μL/well) and incubated for 1-2 hours at 37° C. The wavelength for measuring absorbance of the formazan product was 440 nm.

Western Blotting: Cell lysates were resolved on polyacrylamide gels and transferred to nitrocellulose membranes (Bio-Rad). Membranes were probed with anti-IkBα (1:500 dilution, Santa Cruz) or anti-β-actin (1:5000 dilution, cell signaling) primary antibodies followed by incubation with appropriate HRP-conjugated secondary antibodies (Amersham Biosciences). Blots were analyzed using the Enhanced Chemiluminescence Detection kit (Amersham Biosciences). We also conducted an ELISA to detect TNFα. This assay was performed according to the manufacturer's protocol (R&D Systems, Minneapolis, Minn.).

AFM Measurement: For testing by atomic force microscopy (AFM), a drop of NPs made of PLA-PEG-OH suspension was deposited onto a freshly cleaved mica slide and dried overnight at 25° C. The images were taken using a SPA 400 AFM (Seiko instruments Inc., Japan) at tapping mode using high resonant frequency (Fo=150 kHz) pyramidal cantilevers with silicon probes at a scan frequency of 1 Hz.

Preparation of Gold Chips Used to Detect SPR: For SPR experiments, we used gold films coated onto BK7 glass slides (Biosensing Instruments, Tempe, Ariz.). Each chip is a glass surface coated with a gold layer (47 nm thick) over an intermediate layer of chromium (2 nm in thickness). After each gold chip was cleaned with pure ethanol and dried under a stream of $N_2$, 15-20 µl of cystamine dihydrochloride (20 mM; Sigma, St Louis, Mo.) was cast onto each film overnight in a humidified reaction chamber. Cystamine dihydrochloride is light-sensitive, and the chamber was thus covered with a lid. Next, each chip surface was thoroughly rinsed with deionized water and dried by gentle blowing with a stream of $N_2$ (Yao et al., *Analytical Biochem.* 354: 220-228, 2006). We prepared a fresh mixture of 15 mM N-hydroxysuccinimide, 75 mM 1-ethyl-3-(3-dimethylaminopropyl) carbodiimide, and 6 mg/ml carboxymethyldextran (Sigma, St. Louis, Mo.) and added this mixture to chips modified with cystamine dihydrochloride followed by incubation in a humidified chamber for at least 3-5 hours (often overnight). We next rinsed and dried each chip surface under a stream of $N_2$ (Yao et al., *Analytical Biochem.* 354:220-228, 2006)).

After placing a chip into the BI-2000 SPR machine, we coated NPs PLA-PEG covered with the Fab' fragment of F4/80 Ab onto a gold film after preactivation with 1-ethyl-3-(3-dimethylaminopropyl) carbodiimide/N-hydroxysuccinimide solution. This step was repeated until the NPs coating level permitted the conduct of SPR experiments (Δ ~60-80 mDeg). Two fluidic channels can be used on this instrument, and the same sample plug flowed from the first to the second channel. When "serial mode" is selected, the BI-2000 machine coats simultaneously both channels with the same amount of NPs. This option is essential to permit comparison of the interaction between NPs and the two different types of cells (RAW 264.7 or CACO2BBE cells). Residual activated carboxyl groups were neutralized by a final injection of 1 mM ethanolamine (Sigma). For analysis, injection of RAW 264.7 cells was performed with "single mode" selected on channel 1. For comparison, the same protocol was used injecting CACO2BBE cells selecting single mode on channel 2.

Association and dissociation constants of interactions between NPs linked to the Fab' fragment (coated molecules) and RAW 264.7 cells or CACO2BBE cells (circulating molecules) were obtained using a BI-2000 (Biosensing Instruments) using SPR theory. $K_d$ values (expressed in mol/liter$^{-1}$), which measure the 50% adsorption levels of CMs onto gold chips covered with coated molecules, are commonly used to describe the affinity between two molecules, such as how tightly a ligand binds to a particular receptor. In our study, the software calculation model using 1:1 assumption as ligand:receptor ratio was not used. As cells expressed many receptors on their surface, attributing one interaction to only one cell would have been a mistake. Although the interaction between cells and NPs lead to a resonance deviation angle that can be used to compare quantitatively the interaction strengths of the two types of cells with the NPs. These affinities are influenced by non-covalent intermolecular interactions between the two molecules, including hydrogen-bonding, electrostatic interactions, and hydrophobic and Van der Waals forces. Briefly, after coating a chip with NPs, increasing concentrations of cell solutions in PBS were passed over the chip. A two-step interaction curve was obtained. The first step involved adsorption of cells to the maximal level. In the second step, when the flow of cells concentration returned to zero, nonspecific adsorbed cells are released with the running buffer. On the chip, only coated cells remained "attached." The adsorption curve kinetics thus decreased to a plateau located at a level above the initial base line. The amplitude of cells binding to coated NPs was taken to be the difference between the initial and final levels. The different amplitudes obtained for various cell types at different cellular concentrations were then compared to each other.

Flow cytometry analysis: The following antibodies were used: CD45-PerCP (30F11; BD), CD11c-allophycocyanin (N418; eBioscience), MHC II (I-Ab)-Alexa Fluor 700 (M5/114.15.2; eBioscience), CD11b-eFluor 450 (M1/70; eBioscience), and F4/80-PE-Cy7 (BM8; eBioscience). Dead cells were identified using the fixable Aqua Dead Cell Staining Kit (Invitrogen).

Isolation of total colon cells: Isolation of colonic intestinal cells was performed as previously described with modifications (Denning et al., *Nature Immunol.* 8:1086-1094, 2007). Briefly, large intestines were removed, carefully cleaned and opened longitudinally, washed of fecal contents, and cut into pieces 0.5 cm in length. The tissue was minced and incubated for 11 minutes in HBSS with 5% FBS, 1.5 mg/ml collagenase VIII (Sigma-Aldrich), and 40 U/ml DNase I (Roche) at 37° C. with agitation. Cell suspensions were collected and passed through a 100-µm strainer and pelleted by centrifugation at 300×g.

Flow cytometry: Isolated intestinal colonic cells were resuspended in PBS containing 5% FBS. Live cells were identified using an Aqua Dead Cell Staining Kit accordingly to the manufacturer's instructions, and Fc receptors were blocked with the antibody anti-FcγRIII/II (2.4G2) for 15 minutes at 4° C. After incubation, the cells were stained at 4° C. for 30 minutes with labeled antibodies. Abs used for analysis were from eBioscience unless otherwise noted: FITC-siRNA NPs, PE-conjugated anti-mouse CD 103 (BD Pharmingen), PerCP-conjugated anti-mouse CD45 (BD Pharmingen), PE-Cy7-conjugated anti-mouse F4/80, allophycocyanin-conjugated anti-mouse CD 11c, Pacific blue-conjugated anti-mouse CD11b, and Alexa Fluor 430 (live/dead stain; Invitrogen). Samples were then washed twice in PBS containing 5% FBS and analyzed immediately. Flow cytometric analysis was performed on a LSR II (BD).

Ly6g staining: 5-µm paraffin-embedded tissue sections were deparaffinized in xylene and rehydrated using an ethanol gradient. Tissue sections were incubated with 3% hydrogen peroxide in PBS for 30 minutes at room temperature. Epitope retrieval was performed by treating the tissues with 10 mM sodium citrate buffer (pH 6.0) with 0.05% Tween 20 at 100° C. for 10 minutes in a pressure cooker. Ly6g staining sections were blocked with 10% normal goat serum with 1% BSA in TBS for 2 hours at room temperature followed by incubation with rat monoclonal anti-Ly6g antibody (1: 500 dilution) (Abcam, Cambridge, Mass., USA. ab25377) in TBS with 1% BSA at 4° C. overnight. Tissue sections were treated with their respective biotinylated secondary antibodies for 45 minutes at room temperature (Vector laboratories PK-6101 and BA-9400). Color was developed using the Vectastain ABC kit (Vector Laboratories) followed by DAB reaction. Sections were then counterstained with hematoxylin and dehydrated in ethanol and xylene. Images were acquired at 20× magnification using an Olympus microscope equipped with a D-26 color camera.

Statistical Analysis: Data are expressed as the mean±S.E. Statistical analysis was performed using the unpaired two-tailed Student's t test featured in inStat version 3.06 (GraphPad) software. $p<0.05$ was considered statistically significant.

Results: With regard to the synthesis and characterization of the polymer, PLA-PEG-maleimide, our NP matrix consisted of a poly(lactic acid)poly(ethylene glycol) block copolymer (PLA-PEG). To covalently attach the Fab' fragment of the F4/80 antibody onto the NP surface, we added a reactive functional group (maleimide; Mal) to the PEG side of the PLA-PEG block. Mal enables any molecule containing thiol groups (—SH) to be covalently plugged to the copolymer. The reaction of L-lactide with PEG-Mal was designed to be stoichiometric and total, and all maleimide functional groups were conferred to the block polymer. The PLA-PEG linkage was synthesized by ring-opening polymerization in dry toluene, and the products were precipitated and recovered. We used methoxyPEG and PEG-Mal to initiate the polymerizations of methoxyPEG-PLA (PLA-PEG-OH) and maleimide-PEG-PLA (PLA-PEG-Mal), respectively. Performed in an organic solvent (toluene), this method allowed us to control the length of the PLA chain and ensure a low polydispersity of the polymer's molecular weight (Bouillot et al., *International J. Pharmaceutics* 181:159-172, 1999). The maleimide signal peak did not appear at 6.7 ppm, indicating that maleimide functional groups were not conferred to the control copolymer (PLA-PEG) block, which we then used to synthesize control NPs with no Ab on the surface. The spectrum showed a significant peak at 6.7 ppm, indicating that functional maleimide groups had been connected to the (PLA-PEG). This copolymer was used to synthesize Ab-coated NPs. The NMR spectra confirmed the syntheses of both copolymers and allowed us to calculate the ratio of maleimide/PEG. The maleimide proton signals were observed at 6.69, and the surface area ratio vs. the PEG methylene proton (3.92) was close to that calculated for PEG-Mal. This result allowed us to conclude that the maleimide functional groups were present and intact on the copolymer.

With regard to the generation and characterization of TNFα siRNA/PEI-loaded PLA-based nanoparticles, NPs were prepared with PLA-PEG-OH and PLA-PEG-maleimide by the double emulsion/solvent evaporation method (Laroui et al., *Gastroenterology* 138:843-853 e841-842, 2010; Laroui et al., *Biomaterials* 32:1218-1228, 2011; Laroui et al., *Methods in Enzymol.* 509:101-125, 2012; and Laroui et al., *Biomacromolecules* 8:3879-3885, 2007). As previously described (Laroui et al., *Biomaterials* 32:1218-1228, 2011) and detailed above, TNFα siRNA complexed with polyethyleneimine (10 minutes at 4° C.) can be loaded into NPs (36 μL of 5 mM PEI plus 36 μL of 25 μM siRNA). This inner aqueous phase was added to 4 ml of PLA-PEG-maleimide or PLA-PEG-OH dissolved in dichloromethane to form a first emulsion under sonication. This first emulsion was then mixed with a higher aqueous phase consisting of 8 mL sodium cholate (0.3%). Sodium cholate was chosen as the surfactant because previous work showed that cholate reduced the hydrodynamic diameter and polydispersity index of NPs (Arica and Lamprecht, *Drug Dev. and Industrial Pharmacy* 31:19-24, 2005). The hydrophilicity of PEG and the hydrophobicity of PLA result in a phase separation of the two blocks in water, whereupon the PEG chains orient themselves toward the aqueous phase to form a "corona" layer around the PLA NP matrix (Gref et al., *Advanced Drug Delivery Reviews* 16:215-233, 1995).

The mean size of the TNF-α siRNA/PEI-loaded NPs was found to be about 609 nm for those recovered by PLA-PEG-OH. This size calculation was confirmed by AFM and SEM. The size of NPs PLA-PEG-OH (1 mg/mL) calculated by light scattering was correct, as AFM diameter average was 612 nm. SEM pictures also showed the distribution of NPs PLA-PEH-OH size (1 mg/mL). The polydispersity index (PI) was equal to 0.11. The distribution of our NPs is considered as monodisperse, as the PI is below 0.3.

Various specific antibodies, ligands, and peptide ligand mimetics have been used as nanocarriers to target cells and tissues (Stefanick et al., *ACS Nano*, 2013; and Tran et al., *Carbohydrate Polymers* 92:1615-1624, 2013). Active targeting is intended to cause NPs to accumulate in close proximity to the target cell and actively cross the cell membrane, facilitating the transport of siRNAs into the cytoplasm, where they activate the RNAi pathways. Here, we aimed to use the Fab' fragment of the F4/80 antibody to target TNF-α siRNA-containing NPs to MPs. The removal of the Fc portion of an antibody significantly eliminates its interaction with immune cells and decreases non-specific binding (Lamoyi, *Methods in Enzymol.* 121:652-663, 1986). The separation of the dimeric antigen binding site fragment, $F(ab)_2$, into Fab was achieved by incubation with a reducing agent such as 2-mercaptoethanol; this yielded the Fab portion of F4/80. We then cleaved this Fab to obtain two Fab' fragments of F4/80, as described above. Finally, the Fab' fragment of F4/80 was conjugated to pegylated NPs via the formation of a thioether bond between the thiol groups of the Fab' portion and the maleimide moiety at the distal end of PEG-PLA-maleimide. A reproducible coupling was achieved with a Fab'-to-maleimide ratio of 1:4. Using this strategy, we successfully generated NPs made of PLA-PEG and coated with the Fab' fragment of the F4/80 Ab.

The covalent bonding of the Fab' portion of the F4/80 Ab with PLA-PEG stabilizes the colloidal dispersion, size and repulsion force of the NPs, and enhances their biocompatibility. Physical and biological characterizations of new NPs are needed to optimize them as therapeutic vectors. In the context of colloidal stability, surface repulsion forces are essential to obtaining a homogenous dispersion in an aqueous phase (e.g., PBS or a biological medium). As the addition of the Fab' portion of the F4/80 antibody was the final step after freeze drying the NPs, we were able to test the PLA-PEG-Mal NPs before and after the addition of the Ab fragment. As shown in The PLA-PEG-Mal NPs aggregated significantly in the aqueous phase; this yielded particles larger than 2 μm in diameter could have deleterious biological effects, such as heterogeneous dispersion, inconsistent concentrations, and cell cytotoxicity. However, adding the Fab' portion of the F4/80 Ab to the surface of the NPs completely blocked this unwanted aggregation, likely reflecting the increased hydrophilicity of the coated NPs. This disaggregation increased the degree of maleimide function that could be loaded onto the surfaces of the NPs, which became saturated by the slight excess of the Fab' portion of the F4/80 Ab. SEM confirmed the lack of aggregation among NPs that were coated with the Fab' portion of the F4/80 Ab. The average diameter estimated from the SEM pictures was around 400 nm, whereas the exact measurement by light scattering indicated that the Fab'-covered PLA-PEG NPs had a diameter of about 376 nm. SEM also showed a homogenous distribution and no aggregation of these particles, indicating that the repulsion force occurring between Fab' portions of the F4/80 Ab was higher than the force of repulsion between the maleimide functional groups.

Next, we examined the cytotoxicity of the generated NPs in RAW 264.7 cells, with the viability of RAW 264.7 cells cultured in DMEM medium alone (control) set to 100%. The aggregation of non-coated NPs had a dramatically cytotoxic effect on MPs. Only 16.5% survival was seen among MPs that were treated with aggregated NPs, whereas 112% survival was seen among MPs treated with the coated, non-aggregated NPs. PLA-PEG-OH NPs covered with the Fab' portion of the F4/80 Ab but lacking siRNA (another control) did not aggregate and did not exert any cytotoxicity (viability of 104%). Together, the results from our SEM and WST-1 analyses showed us the requirement of consuming all the maleimide functions present on the NPs surface.

Using the Fab' part of the F4/80 Ab to coat the NPs increased their biocompatibility and bioavailability, making them better candidates for potential therapeutic use.

Finally, we examined certain kinetic parameters. The siRNA release kinetics were better for NPs loaded with PEI-complexed siRNA versus naked siRNA. Interestingly, there was no significant difference in the release of siRNA/PEI between PLA NPs and PLA-PEG NPs covered with the Fab' portion of the F4/80 Ab. These kinetic curves showed that our NPs avoided the so-called "burst effect" (i.e., the deleterious early release of the loaded drug).

The above results indicate that the linkage of the Fab' part of the F4/80 Ab is key to obtaining a homogenous suspension of NPs and maintaining cellular integrity. The Fab' fragment provides positive charges that can generate repulsion interactions between the NPs (zeta potential≅±2.56 mV). We mixed the Fab' fragment [initial concentration ($C_{Fab'}$)=201 µg/mL] with 30 mg of PLA-PEG-Mal NPs. Once the reaction was complete, we centrifuged the NPs (5000 g for 45 min) and collected the supernatant containing the non-attached Fab' molecules ($C_{fFab'}$=139.45 µg/mL). Using the initial amount of Fab' fragments introduced and the amount of non-adsorbed fragments, we estimated the amount of Fab' attached to the NPs as:

$$n_{NP} = \frac{6 m_{NP}}{\pi D^3 \rho}$$

where $n_{NP}$ was the number of NPs; $m_{NP}$ was the mass of the NPs; D was the diameter of the NPs; and p was the volumetric mass of the NPs. For 30 mg of NPs, we calculated $n_{NP}$=9.89*10$^{11}$ particles. Next, we estimated the number of Fab' fragments adsorbed on 30 mg of NPs (300 µL of Fab') as:

$n_{Fab'} = V(C_{iFab'} - C_{fFab'})/M_{wFab'}$ $n_{Fab'} = 3.3*10^{11}/55000$ $n_{Fab'} = 2.05*10^{15}$ Fab' molecules Finally, we calculated the final amount of Fab' molecules per NP ($N_{Fab'}$) as:

$$N_{Fab'} = \frac{2.05*10^{15}}{9.89*10^{11}} = 2073$$

This calculation revealed that there were approximately 2073 Fab' molecules per NP.

PLA-PEG NPs coated with the F4/80 antibody preferentially interact with RAW 264.7 cells over Caco2 BBE cells. The above experiments showed that the NPs were significantly covered with the Fab' portion of F4/80, which reduced the repulsion force between NPs. To confirm this and check the integrity of the Fab' part of the F4/80 Ab, we used surface plasmon resonance (SPR) experiments in which the gold chip was coated with a single layer of NPs. Briefly, the gold chip was covered with a layer of carboxydextran (6 mg/mL in degased water), and the carboxyl group was activated with EDC/NHS (15 mM/75 mM in degased water), so it could then react with any —NH$_2$ functional group-bearing molecule injected into the system. Thus, the NPs covered with the —NH$_2$-bearing Fab' portion of the F4/80 Ab should covalently bind to the activated carboxydextran surface, whereas the PLA-PEG-OH NPs should not. To avoid any interference with NP-released products containing —NH$_2$ functional groups (PEI, siRNA, etc.), we worked exclusively with empty NPs. The flow was optimized at 30 µL/min to allow enough time for the Fab' portion of the F4/80 Ab to react with the activated carboxydextran. Control NPs made of PEG-OH and lacking —NH2 groups did not shift the resonance angle. In contrast, a resonance angle shift of 91 mDeg was observed when we applied two successive injections of Ab-coated NPs, indicating that the Fab' portion of the F4/80 Ab was covalently attached to the gold chip surface.

Next, we assessed whether the Fab' part of the F4/80 Ab retained its intact tridimensional conformation and proper biological activity upon binding to the NPs. To test this, we performed a second SPR experiment using RAW 264.7 cells, which are known to widely express F4/80 receptors (Gordon, *Immunol. Lett.* 65:5-8, 1999; van den Berg and Kraal, *Trends in Immunol.* 26:506-509, 2005; and Gordon et al., *Eur. J. Immunol.* 41:2472-2476, 2011). As control, we used Caco2 BBE (human epithelial) cells that do not express the mouse F4/80 receptor. The SPR experiments were performed in a PBS cell suspension instead of regular cell medium to avoid interference from —NH$_2$-containing molecules. First, we showed that the Ab-coated NPs were covalently attached to the surface. At the end of the first step, both channels were equally covered with Fab'-covered NPs. Then, a second step was performed using the "single" injection mode. In this second step, increasing concentrations of RAW 264.7 cells (channel 1) and Caco2 BBE cells (channel 2) were successively injected onto the Fab'-coated NP-bearing activated carboxydextran surface. The flow rate (35 µl/min) and cell concentrations were optimized with respect to the adsorption kinetics of the cells and NPs, allowing the cells to "roll" across the NP-bound surface and interact with any potential surface receptors. A sensorgram showed the results from two different concentrations of RAW 264.7 cells (2,500 and 7,500 cells/mL); the absolute values of resonance laser deviation were 13 and 33 mDeg, respectively. As mDeg is directly correlated to the binding between the RAW 264.7 cells and the NPs. Between the testing of each cell concentration, the NPs were subjected to a mild regeneration with NaOH (0.01 M); this removed cells and debris that only weakly interact with the NPs (e.g., via hydrogen bonds, hydrophobic interactions, weak electrostatic interactions, etc.) compared to the strong covalent interaction between the NPs and the gold chip. The resonance angle deviations (mDeg) for each NP type and cell concentration. The Ab-coated NPs showed significantly higher interactions with the RAW 264.7 cells compared to the Caco2 BBE cells (13, 17, 33 and 42 mDeg versus 2, 5, 7 and 10 mDeg, respectively, for injected cells concentrations of 2.5k, 5k, 7.5k and 10k cells/mL). As the receptor/antibody interaction is strictly correlated to tridimensional requirements, these results indicate that the integrity of the Fab' portion of the F4/80 Ab was preserved following covalent attachment to the NP surface. As the reaction between maleimide and the Fab' portion of F4/80 is not site-specific, these experiments were required to verify that the random binding of the Fab' fragment did not attenuate the specificity or efficiency of this interaction.

Our in vitro experiments also showed that the Ab-coated NPs had a significantly higher interaction with RAW 264.7 cells compared to Caco2 BBE cells. As the kinetic modeling software used in the present work assumed a basic 1:1 stoichiometric interaction between the ligand and receptor, we were not able to calculate the absolute K (kinetic of interaction) between the NP-bound Fab fragment and the F4/80 receptors on the cells. In sum, our SPR experiments validated one of the main goals of this study by showing that NPs coated with the Fab' portion of the F4/80 Ab are suitable and efficient for MP targeting.

Fab'-coated NPs show increased endocytosis into RAW 264.7 cells. Next, we studied the kinetics of NP phagocytosis by RAW 264.7 cells in vitro. As shown previously (Laroui et al., *Biomaterials* 32:1218-1228, 2011), the phagocytosis of NPs by MPs occurs quickly, and MPs may be saturated with FITC-tagged siRNA/PEI-loaded NPs within one hour (Laroui et al., *Biomaterials* 32:1218-1228, 2011). Here, we examined the effect of the Fab' portion of the F4/80 Ab on the uptake of NPs by MPs, using a short exposure time (15 minutes) in a dynamic system wherein cells were placed in an incubator (5% $CO_2$ and 37° C.) and subjected to mechanical agitation (200 Hz) to reduce/eliminate the phagocytosis of NPs related to cell sedimentation. Thus, our fluorescent microscopic study focused on the NPs that were phagocytosed after interacting with the F4/80 receptors on the MPs. NPs loaded with FITC-tagged siRNA and covered with the Fab' portion of F4/80 (500 µg/mL) showed a higher uptake by MPs compared to non-coated NPs (500 µg/mL). To confirm these observations, we selected more than 50 regions of interest (ROIs) and quantified the fluorescent intensity. The results from three representative ROIs (ROI-001, -002 and -003 for covered and non-covered NPs) were obtained. To enable comparison across different conditions, we report the average intensity by cell surface area. The calculations were first verified by comparing the values obtained for the cell surface and perimeter. The cell surface and perimeter were determined to be 319 $\mu m^2$ and 114 µm, respectively, for cells in contact with Ab-coated NPs, while those for cells in contact with non-coated NPs were 388 $\mu m^2$ and 142 µm, respectively. These values are within an acceptable size range for RAW 264.7 cells. We examined the average fluorescent intensity per unit of surface area. The fluorescence intensity per surface was significantly higher for RAW 264.7 cells exposed to Ab-coated NPs (51325 AU/$\mu m^2$) compared to those exposed to non-coated NPs (10279 AU/$\mu m^2$). These results indicate that the Fab' portion of F4/80 can boost the phagocytosis of NPs by MPs via a direct interaction between Fab' and the F4/80 receptors on RAW 264.7 cells.

Ab-coated TNFα siRNA-loaded NPs reduce TNF expression in inflamed macrophages. Having observed that Ab-coated siRNA-loaded NPs were more effectively taken up by MPs, we tested whether these siRNA-loaded NPs could downregulate TNFα expression. The MPs were pre-treated overnight with the different NPs (250 µg/mL) and then stimulated with LPS (10 µg/mL for 1 hour) to induce inflammation in vitro, and the secretion of TNFα to the medium was measured by ELISA. Lipofectamine-mediated transfection of siRNA TNFα (at the same concentration used in the NPs; Lipofectamine TNFα siRNA) did not have any anti-inflammatory effect in LPS-stimulated cells. This finding was consistent with our previous report (Laroui et al., *Biomaterials* 32:1218-1228, 2011) and emphasizes the potential value of TNFα siRNA-loaded NPs compared to the direct transfection of siRNA. The controls, which consisted of scrambled siRNA-loaded NPs and empty NPs, also failed to show any anti-inflammatory effect. In contrast, the Ab-coated TNFα siRNA-loaded NPs significantly decreased the level of TNFα secreted from the MPs. Together, our in vitro results show that the coating of NPs with the Fab'portion of F4/80 enhanced the kinetics of uptake by MPs, and loading of the NPs with PEI-complexed TNFα siRNA decreased the amount siRNA required to obtain results similar to those obtained using the conventional method of oligonucleotide transfection.

Hydrogel Encapsulation of Ab-Coated TNFα siRNA-Loaded NPs

To deliver the F4/80 antibody-coated TNFα siRNA-loaded NPs to the colonic lumen, we encapsulated them into a biomaterial comprised of alginate and chitosan at a ratio of 7:3 (wt/wt). We previously showed that this biomaterial collapses in intestinal solutions at pH 5 or 6, which reflect the colonic pH under inflamed and non-inflamed states, respectively (Laroui et al., *Gastroenterology* 138:843-853 e841-842, 2010; and Theiss et al., *Inflamm. Bowel Dis.* 17:1163-1176, 2011). Thus, the release of NPs from the hydrogel will occur mostly in the colonic lumen rather than other parts of the gastrointestinal tract, such as the stomach or small intestine (Laroui et al., *Gastroenterol.* 138:843-853, 2010; and Theiss et al., *Inflamm. Bowel Dis.* 17:1163-1176, 2011). First, we needed to confirm that our Ab-coated NPs could be evenly dispersed in the alginate/chitosan hydrogel, as this is essential for in vivo applications (Laroui et al., *Biomaterials* 32:1218-1228, 2011; and Laroui et al., *Methods in Enzymol.* 509:101-125, 2012). We dispersed the NPs in the alginate/chitosan matrix and then, according to the protocol of NP gavage for colon delivery (Hamed et al., 2009), chelated the COO⁻ of the alginate and the $NH_3^+$ of the chitosan with a mixture of $Ca^{2+}$ and $SO_4^{2-}$. After encapsulation, we cut the material on the transverse plane and processed it for SEM observations. The PLA-PEG NPs did not cluster or agglomerate; instead they were homogenously dispersed in the alginate/chitosan matrix. This finding validated the potential value of the PLA-PEG copolymer as a matrix for a new therapeutic delivery system.

Ab-coated NPs loaded with TNFα siRNA can attenuate DSS-induced colitis in mice. Next, we investigated the potential used of Ab-coated TNFα siRNA-loaded PLA-PEG NPs in vivo. C57BL/6 mice were treated with 3% DSS to induce colonic inflammation. Daily gavages of hydrogel-encapsulated Ab-coated TNFα siRNA-loaded NPs (10 mg/mL) (Laroui et al., *Gastroenterology* 138:843-853 e841-842, 2010) attenuated the weight loss induced by 3% DSS treatment, whereas NPs loaded with scrambled siRNA (NPs-F4/80 scrambled siRNA or NPs naked-scrambled) did not. DSS-treated mice that received Ab-coated TNFα siRNA-loaded NPs showed an average weight loss of 6%, compared to the 15% and 25% weight losses seen in mice that received NPs-F4/80 scrambled siRNA or NPs naked-scrambled, respectively. Similar differences were seen in myeloperoxidase (MPO) activity, which was 0.07 unit/µg of total colon protein for mice that received Ab-coated TNFα siRNA-loaded NPs, compared to 22 and 23 units/µg of total colon protein in mice that received NPs-F4/80 scrambled siRNA or NPs naked-scrambled, respectively. Furthermore, we observed that the Ab-coated TNFα siRNA-loaded more effectively attenuated DSS-induced colitis compared to the corresponding non-coated NPs, as DSS-treated mice that received these NPs showed 6% and 9% weight reductions, respectively, and MPO activities of 0.07 and 0.1 unit/µg of total colon protein, respectively. These measurements showed that TNFα siRNA-loaded NPs covered with the Fab' part of the F4/80 Ab efficiently attenuated DSS-induced colitis.

As TNFα is a major upstream activator of the NFκb pathway, we analyzed the accumulation of the IKβα protein (an inhibitor of NFκb activity) in the colon of DSS-treated mice that received the various NPs. IKβα accumulation was lower in DSS-treated mice that received scrambled siRNA-loaded NPs, whereas it was much higher in mice that received Ab-coated TNFα siRNA-loaded NPs. Thus, the Ab-coated TNFα siRNA-loaded NPs appear to protect IKβα from colonic degradation. The accumulation of IKβα' leads to a significant inhibition of the NFκb pathway.

We extended our observations by histological examinations of mouse colon tissues from these two groups. We observed that mice treated with Ab-coated TNFα siRNA-loaded NPs had less shortening of the colon compared to mice that received control NPs (data not shown). Hematoxylin counterstaining can reveal many of the hallmarks of DSS-induced colitis, such as crypt destruction, mucosal ulceration, erosion, and infiltration of lymphocytes into the mucosal tissue. The colons of DSS-treated mice that received Ab-coated NPs loaded with scrambled siRNA showed multifocal inflammatory cell infiltration into the submucosa, severe denudation of the surface epithelium (erosion), and mucodepletion of glands. In contrast, DSS-treated mice that received Ab-coated TNFα siRNA-loaded NPs showed near-normal colonic histology (FIG. 7G). Furthermore, Ly6g immunostaining showed that Ab-coated TNFα siRNA-loaded NPs dramatically reduced the level of neutrophil infiltration compared to that seen in DSS-treated mice that received Ab-coated scrambled siRNA-loaded NPs. In DSS-treated mice, the administration of Ab-coated TNFα siRNA-loaded NPs maintained the tridimensional organization of colonic epithelial cells and the mucosa, which resembled those seen in water-control mice.

Ab-covered NPs loaded with TNFα siRNA target intestinal MPs. Finally, we examined whether the beneficial effect of Ab-coated NPs was mediated via interactions with F4/80 receptors, by testing whether MPs were the major cell type responsible for phagocytizing the NPs. Non-coated or Ab-coated NPs were loaded with FITC-tagged siRNA (as described for TNFα siRNA loading), encapsulated in hydrogel, and used to gavage DSS-treated mice for one week. We defined several subsets of cells and analyzed colonic MPs, which were identified as CD11c(−)CD11b(+)F4/80(+). Interestingly, 28% of MPs showed positive FITC signals in cultures treated with Ab-coated NPs, whereas only 19% of cells treated with non-coated NPs showed FITC signals. These results confirmed that the overall attenuation of DSS-induced colitis occurred due to the NPs interacting with and being taken up by MPs. We conclude that the Ab coating increased specific uptake by MPs, thus allowing better siRNA release and subsequent attenuation of DSS-induced colitis.

Collectively, our results show that TNFα siRNA/PEI-loaded NPs covered with the Fab' part of the F4/80 Ab could be a useful new tool for specifically delivering oligonucleotides to MPs. As the Fab' linkage is the final step of our synthesis, our design strategy could also be used generically, as we can envision researchers generating any cell-type-specific ligand and using it to coat the NPs.

What is claimed is:

1. A drug delivery vehicle, wherein the vehicle comprises a plurality of nanoparticles, a targeting agent that specifically binds a targeted cell or tissue, a therapeutic moiety, and a hydrogel, wherein the targeting agent and the therapeutic moiety are associated with a nanoparticle of the plurality, thereby forming a core; the targeting agent is grafted to the nanoparticle via maleimide-polyethyleneglycol-poly(lactic acid); the hydrogel is generally peripheral to the core; and the nanoparticles have a polydispersity index (PI) below 0.3.

2. The drug delivery vehicle of claim 1, wherein the nanoparticles have a diameter in the range of about 1-1,000 nm and/or the nanoparticles comprise a naturally occurring polymer or a synthetic polymer.

3. The drug delivery vehicle of claim 1, wherein the nanoparticles comprise a biodegradable polymer or a non-biodegradable polymer.

4. The drug delivery vehicle of claim 1, wherein the targeting agent comprises an antibody, a single chain antibody (scFv), an Fab fragment, an Fab' fragment, or an F(ab')$_2$ fragment.

5. The drug delivery vehicle of claim 1, wherein the targeting agent binds to a cell or tissue within the gastrointestinal tract, the cell or tissue being cancerous, or a macrophage or dendritic cell.

6. The drug delivery vehicle of claim 4, wherein the antibody, scFv, Fab fragment, Fab' fragment, or F(ab')$_2$ fragment specifically binds an extracellular matrix protein.

7. The drug delivery vehicle of claim 1, wherein the therapeutic agent is a polypeptide, a nucleic acid, a radioisotope, a metal suitable for photodynamic therapy, or a non-protein, non-nucleotide chemical compound.

8. The drug delivery vehicle of claim 7, wherein the nucleic acid mediates RNAi or the chemical compound is an anti-inflammatory agent.

9. The drug delivery vehicle of claim 1, wherein the hydrogel comprises alginic acid and/or chitosan.

10. The drug delivery vehicle of claim 1, wherein the therapeutic agent is associated with the nanoparticles by virtue of being dissolve or entrapped therein.

11. The drug delivery vehicle of claim 1, further comprising a detectable label or tag.

12. The drug delivery vehicle of claim 1, wherein the targeting agent is an antibody, scFv, Fab fragment, Fab' fragment, or F(ab')$_2$ fragment that specifically binds F4/80, the therapeutic agent inhibits the expression or activity of TNFα, and the hydrogel comprises alginic acid and/or chitosan.

13. A method of treating a patient who is suffering from an inflammatory bowel disease or colon cancer, the method comprising administering to the patient the drug delivery vehicle of claim 1.

14. A kit comprising the drug delivery vehicle of claim 1 and instructions for use.

15. The drug delivery vehicle of claim 4, wherein the antibody is adalimumab, certolizumab pegol, efalizumab, golimumab, infliximab, or natalizumab; the scFv is an scFv of adalimumab, certolizumab pegol, golimumab, or infliximab; and the Fab, Fab', or F(ab')2 fragment is a target-binding fragment of adalimumab, certolizumab pegol, golimumab, or infliximab.

16. The method of claim 13, wherein:
the nanoparticles have a diameter in the range of about 1-1,000 nm; and/or
the nanoparticles comprise a naturally occurring polymer or a synthetic polymer; and/or
the targeting agent comprises an antibody, a single chain antibody (scFv), an Fab fragment, an Fab' fragment, or an F(ab')$_2$ fragment; and/or
the therapeutic agent is a polypeptide, a nucleic acid, a radioisotope, a metal suitable for photodynamic therapy, or a non-protein, non-nucleotide chemical compound; and/or
the hydrogel comprises alginic acid and/or chitosan; and/or
the therapeutic agent is associated with the nanoparticles by virtue of being dissolved or entrapped therein; and/or the drug delivery vehicle further comprises a detectable label or tag.

17. The method of claim 16, wherein the antibody, scFv, Fab fragment, Fab' fragment, or F(ab')$_2$ fragment specifically binds an extracellular matrix protein.

18. The method of claim 16, wherein the nucleic acid mediates RNAi or the chemical compound is an anti-inflammatory agent.

19. The method of claim 16, wherein the antibody is adalimumab, certolizumab pegol, efalizumab, golimumab, infliximab, or natalizumab; the scFv is an scFv of adalimumab, certolizumab pegol, golimumab, or infliximab; and the Fab, Fab', or F(ab')2fragment is a target-binding fragment of adalimumab, certolizumab pegol, golimumab, or infliximab.

20. The kit of claim 14, wherein:
   the nanoparticles have a diameter in the range of about 1-1,000 nm; and/or
   the nanoparticles comprise a naturally occurring polymer or a synthetic polymer; and/or
   the targeting agent comprises an antibody, a single chain antibody (scFv), an Fab fragment, an Fab' fragment, or an F(ab')$_2$ fragment; and/or
   the therapeutic agent is a polypeptide, a nucleic acid, a radioisotope, a metal suitable for photodynamic therapy, or a non-protein, non-nucleotide chemical compound; and/or
   the hydrogel comprises alginic acid and/or chitosan; and/or
   the therapeutic agent is associated with the nanoparticles by virtue of being dissolved or entrapped therein; and/or
   the drug delivery vehicle further comprises a detectable label or tag.

21. The kit of claim 20, wherein the antibody, scFv, Fab fragment, Fab' fragment, or F(ab')$_2$ fragment specifically binds an extracellular matrix protein.

22. The kit of claim 20, wherein the nucleic acid mediates RNAi or the chemical compound is an anti-inflammatory agent.

23. The kit of claim 20, wherein the antibody is adalimumab, certolizumab pegol, efalizumab, golimumab, infliximab, or natalizumab; the scFv is an scFv of adalimumab, certolizumab pegol, golimumab, or infliximab; and the Fab, Fab', or F(ab')2fragment is a target-binding fragment of adalimumab, certolizumab pegol, golimumab, or infliximab.

* * * * *